United States Patent [19]
Gabby et al.

[11] 3,936,391
[45] Feb. 3, 1976

[54] HYDRATED POLYGLYCEROL ESTER COMPOSITION

[75] Inventors: John Lester Gabby; Dennis Dale Corbin; Jack Bruner Lowe, all of Evansville, Ind.

[73] Assignee: Drackett Company, Cincinnati, Ohio

[22] Filed: Feb. 13, 1974

[21] Appl. No.: 442,015

Related U.S. Application Data

[60] Division of Ser. No. 153,837, June 16, 1971, Pat. No. 3,809,764, which is a continuation-in-part of Ser. No. 74,211, Sept. 21, 1970, abandoned.

[52] U.S. Cl. ............. 252/356; 252/305; 252/307; 252/DIG. 1; 264/13; 424/73
[51] Int. Cl.² ........................................... B01F 17/34
[58] Field of Search ................................. 252/356

[56] References Cited
UNITED STATES PATENTS

| | | | |
|---|---|---|---|
| 2,052,025 | 8/1936 | Harris | 252/356 X |
| 3,034,898 | 5/1962 | Kuhrt et al. | 252/356 X |
| 3,582,357 | 6/1971 | Katz | 426/564 |
| 3,592,663 | 7/1971 | Brunner et al. | 426/380 X |
| 3,620,769 | 11/1971 | Peterson | 426/89 X |
| 3,628,968 | 12/1971 | Noznick et al. | 426/570 |
| 3,637,774 | 1/1972 | Babayan et al. | 260/410.6 |
| 3,702,307 | 11/1972 | Norris | 252/356 |
| 3,800,036 | 3/1974 | Gabby et al. | 426/164 |
| R21,322 | 1/1940 | Harris | 252/356 X |

FOREIGN PATENTS OR APPLICATIONS
650,773   3/1951   United Kingdom ............ 426/164

OTHER PUBLICATIONS
Nash et al.: "Polyglycerol Esters", Bakers Digest, Oct. 1963, pp. 72–75.

Primary Examiner—Richard D. Lovering
Attorney, Agent, or Firm—Robert E. Carnahan; Robert H. Uloth

[57] ABSTRACT

An improved polyglycerol ester emulsifier is prepared by heating a polyglycerol ester having 3 to 10 glycerol units and 1 to 2 saturated fatty acyl ester groups each having 16–20 carbon atoms, glycerol and water at a temperature of from 125°F. to 135°F. until a homogeneous paste-like consistency is imparted thereto.

9 Claims, No Drawings

HYDRATED POLYGLYCEROL ESTER COMPOSITION

CROSS REFERENCE TO RELATED APPLICATIONS

This application is a divisional of U.S. Pat. application Ser. No. 153,837 filed June 16, 1971 and now U.S. Pat. No. 3,809,764, patented May 7, 1974 which is a continuation-in-part of U.S. application Ser. No. 74,211 filed Sept. 21, 1970, and now abandoned.

FIELD OF THE INVENTION

This invention involves foods of the low calorie type which resemble butter, margarine, cheese spreads, desserts, frozen desserts including ice cream, whipped cream, dips, puddings, icings, salad dressings, or sauces for use in special diets where a low fat or low calorie intake is desired. The products may broadly be described as gas-in-water emulsions or foams which depend for their character on the use of specific emulsifying agents and stabilizers.

BACKGROUND OF THE INVENTION

Within the last ten years a large body of art has developed involving the formulation of dietary products for weight control purposes particularly for consumption by obese individuals. Development has taken two directions. One has involved the formulation of dietary products providing in themselves complete nutrition so that an obese individual could substitute a measured quantity of such products for his normal food. In this way convenient and accurate control of caloric intake was possible, and yet adequate nutrition was maintained with respect to protein, fat, carbohydrate, vitamin, and mineral intake.

Other developments have not involved nutrition as such, but rather the preparation of imitation foods having very low caloric value yet which closely resemble conventional food products. Such products are attractive for weight control diets and other special diets for the restriction of fats, carbohydrate, salt, residue, etc. since they may be ingested in substantially unlimited quantities and are useful for consumption when eating as a social activity rather than one simply to maintain life. They provide a gustatory pleasure of consuming various types of foods which would otherwise be unavailable or restricted because of the requirements of the special diet. The present inventionn involves compositions of this latter type.

The compositions of the present invention may be classified as imitation butter, margarine, cheese spreads, dips, frozen desserts including ice cream and sherbert, puddings, icings, salad dressings, sauces, and the like. They depend largely for their character on the polyglycerol fatty esters as emulsifiers or foaming agents. The latter substances are accepted as food additives under Title 21, Code of Federal Regulations, Section 121.1120. They have been known for many years having been first described in the chemical literature as early as 1930. Improved polyglycerol fatty esters are described in Belgian Pat. No. 623,179 published Apr. 4, 1963 (Chemical Abstracts 60. 13803$b$). The polyglycerol esters have been widely used in margarine manufacture as anti-spattering ingredients and in the preparation of shortening compositions for use in the preparation of confections and pastries because of their emulsifying qualities. Refer for example to U.S. Pat. No. 3,230,909 and Belgian Pat. No. 656,949 dated June 10, 1965 (Chemical Abstracts 65, 6204$d$).

SUMMARY OF THE INVENTION

The compositions of the present invention are aqueous foams of various densities containing up to 55% by weight of non-aqueous ingredients in the liquid phase and containing as emulsifier or foaming agent from 0.33 to 7.5% by weight of a polyglycerol fatty ester and as stabilizer for the emulsion from 0.2 to 3% by weight of a hydrophilic colloid. The products preferably contain additional ingredients such as flavoring, coloring, dispersing and bodying ingredients as may be required to provide the desired physical and organoleptic qualities. For example, in the preparation of a product resembling whipped cream small amounts of sugar or artificial sweetener, cream flavor and in some instances vanilla flavor are included. In any event, such supplementary ingredients are present in such amount that the total composition of the aqueous phase contains no more than 55% by weight of non-aqueous ingredients.

Suitable products can be prepared employing as little as from 0.33 to 2% of polyglycerol fatty ester as emulsifier but the resulting foams are rather grainy, large-celled, and unstable when whipped to maximum expansion. When whipped to less than maximum expansion, satisfactory texture can be obtained. For products where maximum expansion on whipping is used, it is preferred to use at least about 2% by weight of polyglycerol fatty ester and higher concentrations up to about 7.5% depending upon the desired texture or fat-like quality to be achieved. If approximately 5% by weight of polyglycerol fatty ester is employed a spread resembling whipped butter or a cheese spread is obtained. With a lesser amount of polyglycerol fatty ester, for example about 3%, the oleaginous character diminishes and a lighter product resembling whipped cream is obtained. The preferred polyglycerol ester concentration range for spreads and whipped toppings is 2% to 5% by weight. For frozen deserts such as imitation ice cream, ice milk, or sherbert where a much lower degree of expansion is desired, e.g. 50–110% (0.50 to 1.1 fold), from 0.5 to 1.0% by weight of emulsifier is preferred and the degree of expansion is controlled by the amount of whipping or mixing.

The foregoing spreads and whipped toppings are stable only for a short period unless a hydrophilic colloid is included in the composition as stabilizer. Suitable hydrophilic colloids include the vegetable gums such as acacia gum, xanthan gum, or other well known gums such as locust bean gum and carrageenan. Other hydrophilic colloids that are suitable are water soluble proteins such as gelatin, and water dispersible polysaccharides such as pectin, carboxymethylcellulose, starch (preferably pregelatinized), etc. The simple disaccharides or trisaccharides such as sucrose which form true solutions are not considered hydrophilic colloids for present purposes.

The hydrophilic colloid ingredient is used in an amount ranging from 0.2 to 3% by weight of the aqueous phase. In addition to acting as stabilizers they also improve the texture of the final whipped product. For instance, with imitation ice creams the stabilizer also serves the function of delaying or preventing undesired crystallization of ice or sugars, etc. For these products the amount of stabilizer is limited to about 0.2 to 0.5% by weight to avoid so-called "melt resistance". For ice cream, a liquid melt is desired and excess stabilizer prevents this with formation of a stiff, pudding-like melt. A more complete list of suitable hydrophilic colloids is published in "Handbook of Food Additives," Chemical Rubber Publishing Company, Cleveland, Ohio, 1968, page 315.

The most preferred polyglycerol ester for use in the present invention is triglycerol monostearate. Other polyglycerol esters having from 3 to 10 glycerol units in the polyglycerol chain and 1 or 2 saturated fatty ester groups are, however, operable. The preferred fatty esters are the stearate esters but the palmitate and arachidic esters are also operable. The latter fatty acyl groups contain respectively 16 to 20 carbon atoms. A suitable polyglycerol monostearate (chiefly the triglycerol product) for use in this invention is Durkreme 310 of the Durkee Division of S.C.M. Company. Other useful polyglycerol esters are Drewpol 6-2-S and Drewpol 12-2-S of Drew Chemical Corporation. These are respectively hexaglycerol distearate and decaglycerol distearate.

Polyglycerol fatty esters are wax-like solids which are rather inconvenient to handle in manufacturing operations. They may be melted and blended with some of the other ingredients at a temperature of about 160° F. or higher. We have found it convenient to convert the waxy polyglycerol fatty esters into a finely comminuted condition which makes possible dry blending thereof with other ingredients. One means used to accomplish this is by melting the polyglycerol fatty ester and then passing the molten ester through a spray dryer operated with cold air (30° C. or less) as cooling medium. This results in conversion of the molten material into a fine spray and solidification of the individual droplets to provide a discrete particulate solid. Sometimes other ingredients are mixed or suspended in the molten emulsifier prior to spray cooling. The particulate nature and foaming qualities are unaffected by incorporation of up to 10% by weight of water. Lecithin, may be incorporated at this point to improve the texture of the final foam product. If an anti-caking ingredient is used such as sodium silicoaluminate, up to 12% may be incorporated before spray cooling.

Preparation of the whipped toppings or spreads involves rapidly agitating or whipping the polyglycerol fatty ester with the amount of water selected for the particular batch at a temperature in the range of 125° F. to 212° F. The object of heating within this temperature range is to hydrate and disperse the polyglycerol ester. It has been found that hydration takes place within a rather narrow temperature range of about 125°–135° F. Whipping of the mixture should take place in a mechanical device designed for mixing the air therewith and creating a foam. A suitable device is a household electric mixer operated at relatively high speed and for a sufficient period to produce a foam which does not expand upon further whipping. In practice, all ingredients except the vegetable gum stabilizer are agitated with hot water in the foregoing fashion. Dispersion of the polyglycerol ester thus takes place, but actual hydration thereof is believed to occur as the mixture cools through the temperature range of 125°–135° F.

When a vegetable gum is used as stabilizer it is preferably added as a second stage after full foam development, and mixing is continued just sufficiently to effect dispersion thereof throughout the mixture. Two stage addition of ingredients in this fashion is recommended since the vegetable gums rapidly hydrate and prevent the proper degree of air emulsification when using a simple mechanical mixer if included at the outset. A one stage process according to which all ingredients are incorporated at the outset is, however, operable when using a protein or polysaccharide stabilizer since rapid hydration with the attendant increase in viscosity does not occur with the hydrocolloids other than the vegetable gums.

The resulting product is bland and substantially tasteless although it has the appearance and texture of whipped cream or an oleaginous spread depending upon the concentration of polyglycerol fatty ester employed. In order to mimic conventional food products of the intended types, flavoring, bodying, and coloring agents are employed. For example, imitation butter can be prepared by simply adding a small amount of butter flavor and color and sufficient salt to give the appropriate taste to the foregoing emulsion to obtain a product very closely resembling whipped butter.

For the preparation of products resembling whipped toppings or desserts, a bodying ingredient is sometimes employed to provide the appropriate texture. Either nutritive or non-nutritive materials can be used for this purpose. Dextran is an example of a non-nutritive material that is quite suitable. Sugar is preferred for lending body and texture to a whipped cream-like product. For the preparation of a chocolate dessert cocoa is employed. For imitation ice cream, non-fat milk solids and sugar are employed. This aspect of the invention is subject to almost infinite variation and selection of appropriate ingredients and combinations are at the choice of the skilled operator. In any event, the total amount of bodying ingredients employed does not exceed 45% by weight of the composition. Suitable bodying ingredients in addition to those mentioned above are fructose, dried egg white, and inulin.

A unique feature of the present compositions is that they are oleaginous in appearance and texture, but contain substantially no fat. Small amounts of fat may, however, be inherently included because of its presence in certain of the ingredients. For example, when cocoa is used as a flavoring and bodying ingredient a small amount of fat is inherently present because it is contained in the cocoa. Again, in the preparation of an imitation cheese dip or peanut butter the natural materials which contain a certain amount of fat are needed for flavoring since artificial cheese and peanut butter flavors are not available. In any event, the amount of fat in the final product does not exceed 5% by weight thereof thus making possible the preparation of low calorie products.

Another means for varying the caloric content is by regulation of the degree of expansion or whipping since the size of a serving portion is ordinarily determined by volume. Each of the compositions of the present invention undergoes a specific amount of expansion on whipping in the air which is related to its composition including the content of polyglycerol ester emulsifier. Generally speaking, the lower the concentration of polyglycerol ester employed the greater the maximum degree of expansion. For example, at the 2 to 3% level a foam resembling whipped cream is obtained in which the amount of expansion is approximately 5 to 6 fold relative to the aqueous solution prior to whipping. At the 5% level of polyglycerol ester a lower degree of expansion of about two fold occurs resulting in a more oleaginous appearing product such as a spread. Further modification of the degree of expansion and thus the density of the final whipped product can be effected by adding a fat or fatty material. This reduces expansion and increases density.

For the frozen desserts such as imitation ice creams where the amount of polyglycerol ester is restricted to the range of 0.5 to 1.0% to balance the requirements of stability and mouth feel, maximum whipping is not employed. Here mixing is continued to an "over run" of 50 to 110% i.e. 0.5 to 1.1 fold expansion.

DESCRIPTION OF SPECIFIC EMBODIMENTS

I. Two-Stage Procedure for Spreads and Toppings. In each of the following Examples A-G, the polyglycerol ester is hydrated and a water dispersion thereof is whipped to a foam or oleaginous appearing emulsion in the first stage. The vegetable gum stabilizers are then mixed with the foam in the second stage.

EXAMPLE A. — IMITATION BUTTER

The following materials are agitated at room temperature by means of a food mixer at high speed setting for about 5 min. until a desirable foam is formed, and no further expansion appears to occur.

| Hot water (160° F.) | 170.0 g. |
|---|---|
| Hexaglycerol Distearate | 10.0 g. |
| Salt | 3.5 g. |
| Butter Flavor and Color | 0.4 g. |

A product having the consistency and appearance of whipped butter results. The following gums are then added as stabilizers and texturizing ingredients and mixing is continued for about 2 min. until a homogeneous appearing product is obtained.

| Gum Acacia | 5.0 g. |
|---|---|
| Xanthan Gum | 0.5 g. |

The emulsion is then stable for several days at room temperature.

EXAMPLE B. - VANILLA WHIPPEPD TOPPING

The following ingredients are added to 170 g. of hot (170° F.) water and whipped with a kitchen mixer for about 5 min. until a foam is formed and no further expansion appears to occur.

| Triglycerol Monostearate | 6.0 g. |
|---|---|
| Nonfat Milk Solids | 5.0 g. |
| Flavors and Colors | 0.20 g. |
| Sodium Saccharin | 0.33 g. |
| Inulin | 5.0 g. |

The following gums are then added as stabilizers and whipping is continued as in Example A.

| Gum Acacia | 1.0 g. |
|---|---|
| Xanthan Gum | 1.0 g. |

EXAMPLE C. — CHEESE FLAVORED CHIP DIP

The following materials are blended with 170 g. of hot water (170° F.) using a kitchen mixer as in Example A.

| Triglycerol Monostearate | 6.0 g. |
|---|---|
| Salt | 5.0 g. |
| Dextran | 10.0 g. |
| Nonfat Milk Solids | 15.0 g. |
| Flavor and Color | 1.0 g. |
| Cheddar Cheese Spread | 20.0 g. |

The following gums are then added and mixing is continued as in Example A.

| Gum Acacia | 1.0 g. |
|---|---|
| Xanthan Gum | 1.0 g. |

EXAMPLE D. — WHIPPED TOPPING

A blend of the following dry ingredients is prepared. When whipped with 170 g. of hot water (160° F.) employing a kitchen mixer as in Example B a foam resembling whipped cream is obtained.

| Decaglycerol Distearate | 6.0 g. |
|---|---|
| Salt | 1.2 g. |
| Fructose | 50.0 g. |
| Cream Flavoring | 0.25 g. |
| Sodium Saccharin | 0.15 g. |

The emulsion thus formed is stabilized by blending as in Example A for about an additional 2 min. with the following gums.

| Xanthan Gum | 2.0 g. |
|---|---|
| Gum Acacia | 2.0 g. |

This product provides about 5½ cups of a topping very closely resembling whipped cream having about 3.2 calories per tablespoonful. It may be readily flavored as desired with various fruit flavors such as strawberry, raspberry, etc.

EXAMPLE E. — CHIP DIP

The following ingredients are whipped with a kitchen mixer at high speed for about 5 min. as in Example A.

| Water | 170.0 g. |
|---|---|
| Triglycerol Monostearate | 6.0 g. |
| Salt | 2.0 g. |
| Dry Rochester Sauce | 1.0 g. |
| Powdered Artificial Vinegar | 2.0 g. |
| Barbecue Seasoning | 12.0 g. |
| Green Onion Flakes | 4.0 g. |
| Dehydrated Minced Onion | 0.3 g. |

The emulsion which is thus formed is stabilized and its texture improved by adding the following materials and blending for an additional 2 min.

| Gum Acacia | 5.0 g. |
|---|---|
| Xanthan Gum | 1.0 g. |

EXAMPLE F. — COMPOSITIONS FOR EXTEMPORANEOUS PREPARATION

Compositions suitable for extemporaneous preparation by the housewife or dietician of products described in the foregoing examples are provided by separately blending and packaging the dry ingredients for each stage in the amounts indicated. The package for the first stage is labeled for mixing with a quantity of warm water corresponding to that indicated in the various examples. The second stage ingredients including the vegetable gums are labeled for subsequent addition after formation of a foam of the desired consistency in the first stage. This is specifically illustrated by Example G.

EXAMPLE G. — CHIP DIP PACKAGED FOR EXTEMPORANEOUS TWO-STAGE PREPARATION

The following ingredients are separately packaged as indicated.

| Package (a) | |
| --- | --- |
| Triglycerol Monooleate | 5.2 g. |
| Sodium Silicoaluminate | 0.3 g. |
| Lecithin | 0.5 g. |
| Chive Seasoning | 6.0 g. |
| Package (b) | |
| Gum Acacia | 5.0 g. |
| Xanthan Gum | 1.0 g. |
| Salt | 3.0 g. |
| Dry Rochester Sauce | 1.0 g. |
| Powdered Artificial Vinegar | 0.7 g. |
| Imitation Sour Cream Flavor | 0.3 g. |
| Fructose | 2.0 g. |
| Chopped Chives | 0.5 g. |

The contents of Package (*a*) are emptied into a mixing bowl containing 170 g. of hot tap water (temperature above 135° F.) and mixed for about 4 min. with an electric mixer at high speed as described in Example B. The contents of Package (*b*) are then added and mixing is continued at high speed for about 1 min. until a smooth product is obtained.

II. ONE STAGE PROCEDURE FOR SPREADS AND TOPPINGS

In each of the following Examples H-J, a protein or polysaccharide hydrophilic colloid stabilizer is used. These ingredients do not interfere with efficient aeration due to rapid hydration as do the vegetable gums, and thus may be included during initial mixing for one stage operation.

EXAMPLE H. — CHOCOLATE DESSERT MIX

The following ingredients are blended in the dry condition. The dry blend is whipped with 170 g. of water at about 160° F. for 5 min. to produce a whipped chocolate dessert similar to chocolate pudding.

| Triglycerol Monostearate | 6.0 g. |
| --- | --- |
| Salt | 1.3 g. |
| Cocoa | 12.0 g. |
| Gelatin | 6.0 g. |
| Sugar | 10.0 g. |
| Nonfat Milk Solids | 5.0 g. |
| Flavor or Color | 0.5 g. |
| Fructose | 24.0 g. |
| Sodium Saccharin | 0.15 g. |

EXAMPLE I. — WHIPPED TOPPING

The following ingredients are whipped with a kitchen mixer at high speed as in Example H.

| Hot Water (170° F.) | 170.0 g. |
| --- | --- |
| Triglycerol Monostearate | 6.0 g. |
| Salt | 1.3 g. |
| Pregelatinized Wheat Starch | 5.0 g. |
| Sugar | 50.0 g. |
| Cream Flavor | 0.25 g. |
| Sodium Saccharin | 0.15 g. |

EXAMPLE J. — COMPOSITIONS FOR EXTEMPORANEOUS PREPARATION

The dry ingredients listed in Examples H and I in the quantities indicated may be individually packaged for extemporaneous preparation of these products in the home upon mixing with hot water as directed in these two examples.

III. EMULSIFIER PASTE FOR COLD WATER USE

An improved emulsifier composition adapted for extemporaneous preparation of the foregoing products using cold water for constitution is provided by the following embodiment of this invention. This emulsifier paste is comprised of a hydrated polyglycerol ester which may be substituted for the polyglycerol esters referred to in the foregoing examples in an amount corresponding to the weight of polyglycerol ester contained therein. The emulsifier paste is prepared by heating a mixture of 3 parts by weight of polyglycerol ester, from 3 to 5 parts by weight of glycerol, and from 1 to 3 parts by weight of water at a temperature in the range of from 125° F. to 135° F. until a homogeneous mixture is produced. The preferred emulsifier paste is prepared from 3 parts by weight of polyglycerol ester, 3 parts by weight of glycerol, and 3 parts by weight of water. In any event, 9 parts by weight of the mixture is employed in preparing the paste. That is, if the proportion of glycerol is increased to 5 parts by weight then the proportion of water is decreased to 1 part by weight. A minor amount of up to about 10% by weight of a microbiological preservative and a vegetable gum stabilizer may be added.

EXAMPLE K. — PREPARATION OF TRIGLYCEROL MONOSTEARATE EMULSIFIER PASTE.

Triglycerol monostearate, 100 parts by weight, is subdivided into shavings by means of a food chopper and mixed with 100 parts by weight of water and 100 parts by weight of glycerol and warmed at 125° – 135° F. for approximately 3 hrs. During this time a smooth homogeneous white cream-like mass is formed as a result of hydration of the triglycerol monostearate and dissolution or dispersion thereof in the glycerol. To serve as microbiological preservative, 0.3 parts by weight of sorbic acid, and 1 part by weight of acetic acid is then added to the mixture. Other preservatives may be substituted. A small amount of xanthan gum, 0.25 parts by weight, is added for physical stability and the mixture is allowed to cool to room temperature. It is packaged in individual air-tight foil envelopes each containing approximately 8 g. of material. This may then be used in the foregoing examples in place of pure triglycerol monostearate on a proportional weight basis relative to the content of triglycerol monostearate.

The foregoing process results in hydration of the polyglycerol ester emulsifier and transforms it into a condition where it possesses equivalent foaming capacity in cold water to that obtained using warm water with the dry polyglycerol ester specified in Examples A–J. This is a distinct advantage for home use since without proper control of the water temperature for hydration of the polyglycerol ester proper emulsification to provide the contemplated whipped product texture may not be achieved.

In packaging the emulsifier paste as part of a unit for use in the home, the paste is kept apart from the other ingredients in a container which is sealed for the exclusion of the atmosphere. The purpose of this is to prevent dehydration since the cold water foaming properties of the emulsifier are dependent upon prior high temperature hydration of the polyglycerol ester in accordance with the foregoing procedure. Other ingredients of the present whipped products when stored in contact with the paste in the same package may have a greater affinity for water than the polyglycerol ester, and the water of hydration may be lost by the emulsifier with the attendant loss of foaming properties. The hydrophilic colloid and bodying ingredients including the vegetable gums, gelatin, dextran, starch, etc. are particularly deleterious when in contact with the hydrated emulsifier in a product packaged for extended storage.

Examples L, M, and N which follow illustrate the preparation of whipped topping (Examples L and N) and chip dip (Example M) products using the foregoing emulsifier paste.

EXAMPLES L, M, AND N — TOPPING FORMULAS EMPLOYING EMULSIFIER PASTE; TWO-STAGE PROCEDURE

The tabulation of ingredients listed below refers to three different formulas for the preparation of products of the present invention according to the cold water method employing the emulsifier paste of Example K. In each instance the quantity of emulsifier paste specified was added to the water specified at room temperature and mixed with an electric mixer at high speed. The remainder of the ingredients were then added with mixing for an additional minute.

| Ingredients | Example L | Example M | Example N |
|---|---|---|---|
| Water | 75.0 g. | 75.0 g. | 75.0 g. |
| Emulsifer Paste (Example K) | 8.0 g. | 36.0 g. | 8.0 g. |
| Gum Acacia | 2.5 g. | 2.5 g. | 2.5 g. |
| Xanthan Gum | 0.5 g. | 0.5 g. | 0.5 g. |
| Salt | 1.5 g. | 1.5 g. | 1.5 g. |
| Powdered Sugar | 40.0 g. | 40.0 g. | 75.0 g. |
| Sodium Bicarbonate | 0.1 g. | 0.3 g. | 0.1 g. |
| Flavoring and Coloring | 0.2 g. | 0.2 g. | 0.2 g. |

AEROSOL TOPPINGS AND SPREADS

The foregoing disclosure has been directed primarily to the preparation of toppings and spreads extemporaneously in the kitchen or home. The following example involves a modification of the blending and whipping steps as described above which can be carried out in industrial equipment to provide a liquid concentrate suitable for delivery from an aerosol container using either nitrous oxide alone or in combination with one of the low-boiling fluorinated hydrocarbons approved for use in aerosol packaging of food products. This modification involves dispersing or dissolving all of the ingredients in the full amount of water to be used in the final product, but accomplishing the dispersion in such a way as to avoid incorporating air and thus obtaining a foam or an air-in-water emulsion as described above. This is accomplished by using a mechanical homogenizer which mixes the ingredients in a closed system and thus avoids the formation of the foam. A foam is subsequently formed on delivery of the composition from the valve of the aerosol container. The following example illustrates this.

EXAMPLE O. — IMITATION BUTTER FOR AEROSOL DELIVERY

The following ingredients are mixed with heating to about 170° F. in a closed vessel having no free air space above the liquid. The blend is then fed to a mechanical homogenizer and the resulting homogenized liquid is used as the liquid phase for an aerosol container.

| | |
|---|---|
| Water | 170.0 g. |
| Triglycerol Monostearate | 8.0 g. |
| Sodium Silicoaluminate | 0.2 g. |
| Gum Acacia | 5.0 g. |
| Xanthan Gum | 1.0 g. |
| Salt | 3.5 g. |
| Butter Flavor and Color | 0.54 g. |

When the foregoing is expelled through the valve of a conventional aerosol container the extruded product forms a foam or emulsion which has the consistency of whipped butter and insofar as organoleptic character is concerned, it is substantially identical with whipped butter. V. Shaving Cream It has been noted that a shaving foam can be prepared by hydration of a polyglycerol ester and whipping with water as has been described above for the various food products. From 2–10% by weight of a water insoluble pulverulent bodying agent such as dextran, cellulose, talc, silica, sodium silicoaluminate, Fuller's earth, clay, etc. is included to provide the appropriate texture to the foam. The hydrophilic colloid foam stabilizer is not required for this product. Suitable perfumes, etc. are included for elegance. A microbiological preservative is used to improve storage stability. This is a highly unique shaving cream since it contains no soap, fat or oil and functions without additional water. Its lubricating action makes possible an extremely close shave and the residue may be wiped off or washed away. It leaves the skin with the feeling of having been treated with cold cream. Example P which follows illustrates the preparation of such a shaving cream.

EXAMPLE P — SHAVING CREAM

Step A.

Glycerol 5.5 g., triglycerol monostearate 5.5 g., and water 5.5 g. is formed into a homogeneous cream-like paste by warming at 135° F. The mixture is then allowed to cool and mixed with 68.3 g. of water, 2.8 of sodium silicoaluminate, 1.4 g. of 5% solution of menthol in alcohol, and 0.03 g. of a preservative consisting of 1 part propylparabens and 4 parts methylparabens (weight basis). The resulting product is used as the liquid fill for an aerosol dispenser. It may also be dispensed in a jar or tube. It is preferred that it be applied to the face or other surface to be shaved without mixing with additional water and with the surface dry.

VI. FROZEN DESSERTS

Three features distinguish the preparation of frozen desserts such as imitation ice cream or sherbert from the preparation of the whipped toppings and spreads described above. First, conventional ice cream making equipment is employed and the degree of expansion of the aqueous formulation on aeration is limited to 0.5 to 1.1 times the original volume. This corresponds to 50–110% overrun in the vernacular of the ice cream art. In preparation of the whipped toppings and spreads, the maximum degree of overrun which the composition will support on continued whipping is employed. In the case of ice creams aeration is not a separate step but rather results from the stirring action of the ice cream freezer during the freezing operation.

Second, the amount of polyglycerol ester emulsifier employed is reduced to 0.5 to 1% by weight of the composition with the preferred amount being 0.8% by weight. The toppings and spreads preferably employ from 2 to 5%. The reduced amount of emulsifier is possible because of the different stability characteristics of the frozen product as compared to the toppings and spreads which are generally served at room temperature or simply at refrigerator temperature. The reduced emulsifier level is desirable to avoid an oleaginous character which is not customary with ice cream, frozen custard, or sherbert.

The third difference is in the amount of stabilizer employed. For imitation ice creams and sherberts it is preferred to use from 0.2 to 0.5% by weight of stabilizer and preferably 0.3% by weight thereof to avoid so called melt resistance. When ice cream or sherbert melts, a liquid should result to afford the proper mouth feel. If an amount of stabilizer in excess of 0.5% is employed a rather stiff pudding-like melt results and this is undesirable. The following examples illustrate preparation of an imitation ice cream and an imitation soft ice cream which contain no fat as such, and less than 1% by weight of the polyglycerol ester emulsifier. Federal standards for products labeled ice cream provide for 8 to 10% by weight of fat.

EXAMPLE Q — IMITATION ICE CREAM

Triglycerol monostearate (Durkreme 310), 8 grams is mixed with 8 grams of water and kept at 125°–135° F. overnight. This and the following ingredients are then mixed with sufficient water to provide a kilogram of mix.

| | |
|---|---|
| Nonfat Milk Solids | 141.3 g. |
| Sugar | 157.3 g. |
| Guar gum | 2.0 g. |
| Carrageenan | 0.5 g. |
| Polysorbate 80 | 0.3 g. |
| Water | q.s. |

This mixture is then pasteurized at 165° F. for 20 seconds, the flavors and colors, 1.9 g., added and the mixture then passed through a homogenizer before loading into a commercial ice cream freezer. It is frozen to a soft paste consistency and then transferred to 5 oz. containers and frozen hard. The ice cream freezer was adjusted to provide for 85% overrun. Other stabilizers such as sodium alginate or gelatin may be substituted for the guar gum. The carrageenan may be omitted.

EXAMPLE R — IMITATION SOFT ICE CREAM

Triglycerol monostearate (Durkreme 310), 8 grams is mixed with 8 grams of water and kept at 125° – 135° F. overnight. This and the following ingredients are then mixed with sufficient water to provide a kilogram of mix.

| | |
|---|---|
| Concentrate Skim Milk | 166.2 g. |
| Sugar | 184.9 g. |
| Guar gum | 2.0 g. |
| Carageenan | 1.0 g. |
| Polysorbate 80 | 0.4 g. |
| Water, | q.s. |

This mixture is then pasteurized at 165° F. for 20 seconds, flavors and colors having a total weight of 2.0 g. are added, the mixture homogenized and loaded into a commercial soft-serve ice cream freezer. The freezer is adjusted to provide a 75% overrun.

While several particular embodiments of this invention have been shown, the invention is not limited thereto since many modifications may be made. It is intended that the appended claims should cover any such modification as falls within the spirit and scope of the invention.

What is claimed is:

1. An improved polyglycerol ester emulsifier prepared by heating 9 parts by weight of a mixture consisting of 3 parts by weight of a polyglycerol ester, from 3 to 5 parts by weight of glycerol, and 1 to 3 parts by weight of water at a temperature in the range of from 125°F. to 135°F. until a homogeneous paste-like consistency is imparted thereto said polyglycerol ester being molecularly constituted of from 3 to 10 glycerol units and from 1 to 2 saturated fatty acyl ester groups each having from 16 to 20 carbon atoms.

2. The product of claim 1 wherein 3 parts by weight of polyglycerol ester, 3 parts by weight of glycerol, and 3 parts by weight of water is employed.

3. The product of claim 2 wherein said fatty acyl ester group of said polyglycerol ester is stearate.

4. The product of claim 1 wherein said polyglycerol ester is triglycerol monostearate.

5. The product of claim 1 wherein said polyglycerol ester is hexaglycerol distearate.

6. The product of claim 1 wherein said polyglycerol ester is decaglycerol distearate.

7. The product of claim 1 having up to 2% by weight of a microbiological preservative incorporated therein.

8. The product of claim 1 when packaged in an airtight container.

9. The product of claim 1 containing a minor amount of a preservative and a stabilizer.

* * * * *